United States Patent [19]
Pees et al.

[11] Patent Number: 5,854,252
[45] Date of Patent: *Dec. 29, 1998

[54] DIHALOTRIAZOLOPYRIMIDINE DERIVATIVES

[75] Inventors: Klaus-Jurgen Pees, Mainz; Heinz-Manfred Becher, Bingen, both of Germany

[73] Assignee: Shell Internationale Research Maatschappij B.V., The Hague, Netherlands

[ * ] Notice: The term of this patent shall not extend beyond the expiration date of Pat. No. 5,612,345.

[21] Appl. No.: 424,535

[22] PCT Filed: Mar. 3, 1994

[86] PCT No.: PCT/EP94/00635

§ 371 Date: Aug. 28, 1994

§ 102(e) Date: Aug. 28, 1994

[87] PCT Pub. No.: WO94/20501

PCT Pub. Date: Sep. 15, 1994

[30] Foreign Application Priority Data

Mar. 4, 1993 [EP] European Pat. Off. ............. 93103464

[51] Int. Cl.[6] ....................... A61K 31/505; C07D 487/00
[52] U.S. Cl. ............................. 514/258; 544/263
[58] Field of Search ............................. 514/258; 544/263

[56] References Cited

U.S. PATENT DOCUMENTS

| | | | |
|---|---|---|---|
| Re. 32,676 | 5/1988 | Eicken et al. | 514/258 |
| 2,553,500 | 5/1951 | Harsh | 544/263 |
| 3,655,896 | 4/1972 | Davies et al. | 544/263 |
| 4,572,910 | 2/1986 | Wade | 514/222 |
| 4,617,303 | 10/1986 | Eicken et al. | 514/258 |
| 5,013,351 | 5/1991 | Jelich et al. | 544/263 |
| 5,593,996 | 1/1997 | Pees et al. | 514/258 |
| 5,612,345 | 3/1997 | Becher et al. | 514/258 |

OTHER PUBLICATIONS

Y. Makisumi, et al. "Studies on Azaindolizine Compounds . . . ", Chem. Pharm.Bull 12(2), 204–212 (1964).
Chem. Abs. No. 61: 2942a, (1964).
Chem. Abstracts, vol. 61, No. 3, 2941g, (1964).
Chem. Abstracets, vol. 117, No. 150806r, (1992).

Primary Examiner—Deborah C. Lambkin
Attorney, Agent, or Firm—Charles F. Costello, Jr.

[57] ABSTRACT

The invention relates to fungicidal compositions which comprise a carrier and, as active ingredient, a dihalotriazolopyrimidine derivative of general formula (I) in which R represents an optionally substituted branched or straight-chain alkyl or alkoxy group or an optionally substituted cycloalkyl, aryl, aryloxy, or heterocyclyl group, and Hal represents a fluroine, chlorine, bromine or iodine atom; and their use as fungicides. Certain of these dihalotriazolopyrimidine derivatives are novel and a process for the preparation of these compounds is also provided.

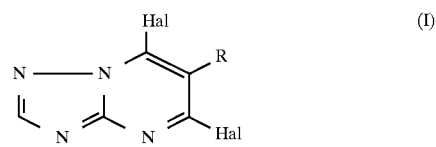

23 Claims, No Drawings

DIHALOTRIAZOLOPYRIMIDINE DERIVATIVES

This application is a 371 of PCT/EP94/00635 filed Mar. 3, 1994.

This invention relates to certain dihalotriazolopyrimidine derivatives, some of which are novel, processes for their preparation, compositions containing such compounds and their use as fungicides.

Chemical Abstracts (1964), 61:2941 g discloses the preparation of 5,7-dichloro-6-methyl-1,2,4-triazolo [1,5-a] pyrimidine by heating 5,7-dihydroxy-6-methyl-2,4-triazolo [1,5-a] pyrimidine with phosphorus oxychloride for 4 hours at 100° C. However, there is no indication that either of these compounds exhibits biological activity.

Applicant's co-pending European application no. 92204097.7 (EP-A-0550113) discloses compounds of the general formula.

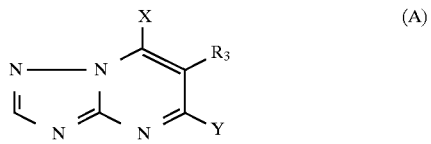

in which $R^3$ represents an optionally substituted aryl group and X and Y both represent a chlorine atom or both represent a bromine atom, as intermediates in the preparation of certain fungicidally active triazolopyrimidine derivatives of the general formula

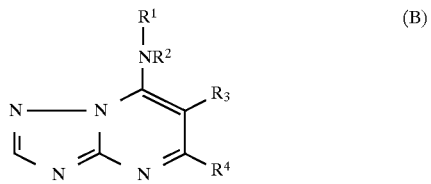

in which $R^1$ represents an optionally substituted alkyl, alkenyl, alkynyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ is as defined above, and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. However, there is no indication in this document that the compounds of formula A themselves possess any fungicidal activity.

It has now been discovered that certain compounds of formula A and certain further novel dihalotriazolopyrimidine derivatives exhibit fungicidal activity in their own right.

According to the invention there is therefore provided a fungicidal composition which comprises a carrier and, as active ingredient, a compound of the general formula

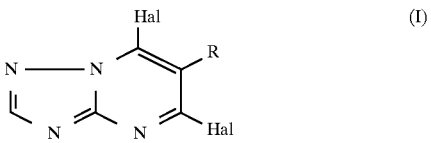

in which R represents an optionally substituted branched or straight-chain alkyl or alkoxy group, or an optionally substituted cycloalkyl, aryl, aryloxy or heterocyclyl group, and Hal represents a fluorine, chlorine, bromine or iodine atom.

When the compounds in the compositions of this invention contain a cycloalkyl group, this may contain from 3 to 8, preferably 3 to 6, carbon atoms. An aryl group may be any aromatic hydrocarbon group, especially a phenyl or naphthyl group. A heterocyclyl group may be any saturated or unsaturated ring system containing at least one heteroatom, 3- to 6-membered rings being preferred and 5- and 6-membered rings being especially preferred. Nitrogen-, oxygen- or sulphur-containing rings, such as pyridinyl, pyrimidinyl, pyrrolidinyl, furyl, pyranyl, morpholinyl and thienyl, are particularly preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, halosulphonyl, carbamoyl, alkylamido, phenyl, phenoxy, benzyl and benzyloxy, heterocyclyl, especially furyl, and cycloalkyl, especially cyclopropyl, groups. Typically, 0–3 substituents may be present.

When any of the foregoing substituents represents or contains an alkyl group, this may be linear or branched and may contain up to 12, preferably up to 6, and especially up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. In the case of cycloalkyl and heterocyclyl groups, optional substituents also include groups which together with two adjacent carbon atoms of the cycloalkyl or heterocyclyl group form a saturated or unsaturated hydrocarbyl ring. In other words, a saturated or unsaturated hydrocarbyl ring may be optionally fused with the cycloalkyl or heterocyclyl group.

It is preferred that R represents a $C_{1-12}$ alkyl, $C_{1-12}$ alkoxy, $C_{3-8}$ cycloalkyl, phenyl, phenoxy or naphthyl group or a 3- to 6-membered heterocyclic ring, each group or ring being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, formyl, $C_{1-4}$ alkoxycarbonyl, carboxyl, halosulphonyl, phenyl, phenoxy, benzyl and benzyloxy groups or, in the case where R represents a $C_{3-8}$ cycloalkyl group or a 3- to 6-membered heterocyclic ring, optionally ortho-fused with a benzene ring.

More preferably, R represents a $C_{1-6}$ alkyl, $C_{1-6}$ alkoxy, $C_{3-8}$ cycloalkyl, phenyl, phenoxy or naphthyl group or a 3- to 6-membered heterocyclic ring, each group or ring being optionally substituted by one or more substituents selected from halogen atoms, $C_{1-4}$ alkyl, $C_{1-4}$ haloalkyl, $C_{1-4}$ alkoxy, $C_{1-4}$ haloalkoxy, halosulphonyl, phenyl, phenoxy and benzyloxy groups.

A particularly preferred sub-group of compounds of formula I is that in which R represents propyl, butyl, ethoxy, cyclopentyl, cyclohexyl, fluorophenyl, chlorophenyl, bromophenyl, dichlorophenyl, chlorofluorophenyl, methylphenyl, propylphenyl, butylphenyl, dimethylphenyl, trifluoromethylphenyl, methoxyphenyl, ethoxyphenyl, dimethoxyphenyl, diethoxyphenyl, trimethoxyphenyl, trifluoromethoxyphenyl, chlorosulphonylphenyl, biphenylyl, phenoxyphenyl, benzyloxyphenyl, fluorophenoxy, chlorophenoxy, methylphenoxy, dimethylphenoxy, naphthyl or thienyl group; and Hal represents a chlorine or bromine atom.

A method of making a composition as defined above is also provided which comprises bringing a compound of formula I as defined above into association with at least one carrier. Such a composition may contain a single compound or a mixture of several compounds of the present invention.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive-component enabling them to be applied directly to the stem of a vine plant.

Certain of the compounds of formula I as defined above are novel. Accordingly, the invention also provides a compound of the general formula I as previously defined with the provisos that. (i) when R represents an optionally substituted aryl group, then both groups Hal do not represent a bromine atom, and (ii) when R represents Hal do not represent a bromine atom, and (ii) when R represents a methyl group, then both groups Hal do not represent a chlorine atom.

The present invention further provides a process for the preparation of a compound of formula I as defined above which comprises (a) reacting a compound of the general formula

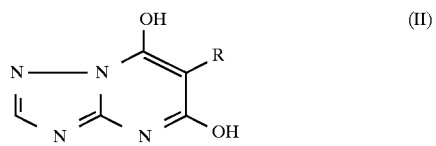

in which R is as defined above, with a chlorinating or brominating agent to produce a compound of formula I in which Hal represents a chlorine or bromine atom;
(b) if desired, reacting the compound of formula I formed in (a) with a fluorinating agent to produce a compound of formula I in which Hal represents a fluorine atom; and
(c) if desired, reacting the compound of formula I formed in (a) with NH₃ and then with diiodomethane in the presence of a diazotising agent to produce a compound of formula I in which at least one Hal represents an iodine atom.

The process of step (a) may be carried out in the presence of a solvent. Suitable solvents include halogenated hydrocarbons, such as dichloromethane. Alternatively, an excess of the chlorinating or brominating agent may serve as a solvent. Suitable chlorinating agents include phosphorus oxychloride, phosphorus trichloride and phosphorus pentachloride. Suitable brominating agents include phosphorus oxybromide, phosphorus tribromide and phosphorus pentabromide. The reaction is suitably carried out a temperature in the range from 0° C. to the reflux temperature of the reaction mixture, the preferred reaction temperature being from 20° C. to the reflux temperature of the reaction mixture.

The process of step (b) is conveniently carried out in the presence of a solvent. Suitable solvents include sulpholane, dimethylformamide or a mixture of acetonitrile and a crown ether. If sulpholane or dimethylformamide is used as solvent, it is advantageous to use toluene as a co-solvent to aid dehydration of the fluorinating agent. The reaction is suitably carried out at a temperature in the range from room temperature (about 15° C.) to the reflux temperature of the reaction mixture, the preferred reaction temperature being from 40° C. to the reflux temperature of the reaction mixture. Suitable fluorinating agents include alkali metal fluorides, especially potassium fluoride, antimony pentafluoride and diethylaminosulphur trifluoride.

The reaction with NH₃ in the process of step (c) is conveniently carried out in the presence of a solvent. Suitable solvents include ethers, such as dioxane, diethyl ether and tetrahydrofuran, halogenated hydrocarbons, such as dichloromethane, and, especially, toluene. The reaction is suitably carried out at a temperature in the range from 20° C. to the reflux temperature of the reaction mixture, the preferred reaction temperature being from 40° C. to the reflux temperature of the reaction mixture. It is also preferred that the reaction is carried out in the presence of a base and, preferably, an excess of NH₃ may serve as the base. The diazotising agent used in step (c) may be any alkyl ester of nitrous acid, isopentyl nitrite being especially preferred. If an alkyl ester of nitrous acid is used, this may also serve as a co-solvent with the diiodomethane. This reaction is suitably carried out at a temperature from 60° C. to 120° C., the preferred reaction temperature being from 70° C. to 110° C. Both stages in the process of step (c) may be performed in one pot.

Compounds of formula II can be prepared by reacting 3-amino-1,2,4-triazole with an appropriate malonic acid ester under alkaline conditions according to the method of Y. Makisumi, Chem. Pharin. Bull, 9, 801, (1961).

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, apples and tomatoes. The duration of protection is normally dependent on the individual compound selected, and also a variety of external factors, such as climate, whose impact is normally mitigated by the use of a suitable formulation.

The invention is further illustrated by the following examples:

EXAMPLE 1

Preparation of 5,7-dichloro-6-(2-chlorophenyl)-5,7-Dihydroxy-6-(2-chlorophenyl)-1,2,4,-triazolo[1,5a]pyrimidine (R=2-chlorophenyl; Hal=Cl)

5,7-Dihydroxy-6-(2-chlorophenyl)-1,2,4-triazolo[1,5a]-pyrimidine (6.2 g, 0.026 mol) and 30 ml of phosphorus oxychloride were mixed and the resulting suspension was refluxed for 3 hours. The excess phosphorus oxychloride was distilled off from the resulting clear solution and the resulting viscous oil was dissolved in 50 ml of dichloromethane. To decompose traces of phosphorus oxychloride in the dichloromethane solution 50 ml of ice water were added carefully. The organic layer was then separated, dried with sodium sulphate and the solvent distilled off in vacuo to give 6.62 g, 5,7-dichloro-6-(2-chlorophenyl)-1,2,4-triazolo-[1,5a]pyrimidine as yellowish crystals, m.pt. 153° C. Yield: 85% of theoretical.

EXAMPLE 2

Preparation of 5,7-dibromo-6-(2-chlorophenyl)-1,2,4-triazolo[1,5a]pyrimidine (R=2-chlorophenyl; Hal=Br)

5,7-Dihydroxy-6-(2-chlorophenyl)-1,2,4-triazolo[1,5a]-pyrimidine (15 g, 0.057 mol) was added in small portions at a temperature of about 100° C. to molten phosphorus oxybromide (excess, 40 g). After a vigorous initial reaction, a clear highly viscous oil resulted which was left at 120° C. for an additional 2 hours. The mixture was cooled to room temperature and the resulting "glass" was added portionwise to a mixture of water and dichloromethane. The organic layer was separated, dried with sodium sulphate and the solvent distilled off in vacuo to give 19.93 g, 5,7-dibromo-6-(2-chlorophenyl)-1,2,4-triazolo[1,5a]-pyrimidine as yellowish crystals, m.pt. 212° C. Yield: 90% of theoretical.

EXAMPLE 3 TO 52

By processes similar to those described in Example 1 above, further compounds according to the invention were prepared as detailed in Table I below. In this table the compounds are filed by reference to formula I.

TABLE I

| Example No. | R | Hal | M. pt (°C.) |
|---|---|---|---|
| 3 | 4-OC₂H₅ phenyl | Cl | 138 |
| 4 | 3-OCH₃ phenyl | Cl | 151 |
| 5 | 2-OCH₃ phenyl | Cl | 143 |
| 6 | 2-SO₂Cl phenyl | Cl | 234 |
| 7 | 3-CF₃ phenyl | Cl | 160 |

TABLE I-continued

| Example No. | R | Hal | M. pt (°C.) |
|---|---|---|---|
| 8 | 4-CH(CH₃)₂ phenyl | Cl | 122 |
| 9 | 4-OCF₃phenyl | Cl | 194 |
| 10 | naphth-2-yl | Cl | 192 |
| 11 | 4-F phenyl | Cl | 206 |
| 12 | 4-OC₆H₅ phenyl | Cl | 160 |
| 13 | 4-biphenylyl | Cl | 170 |
| 14 | 3,4-(OCH₃)₂ phenyl | Cl | 185 |
| 15 | 4-OCH₂C₆H₅ phenyl | Cl | 170 |
| 16 | 2-F phenyl | Cl | 173 |
| 17 | 3-F phenyl | Cl | 227 |
| 18 | 2-Br phenyl | Cl | 176 |
| 19 | 4-Br phenyl | Cl | 190 |
| 20 | 2-OCH₂C₆H₅ phenyl | Cl | amorphous |
| 21 | 2,3-(OCH₃)₂ phenyl | Cl | 150 |
| 22 | 3-Br phenyl | Cl | 205 |
| 23 | naphth-1-yl | Cl | 202 |
| 24 | 2,3-(OC₂H₅)₂ phenyl | Cl | 63 |
| 25 | 3,4-Cl₂ phenyl | Cl | 205 |
| 26 | thien-2-yl | Cl | 160 |
| 27 | thien-3-yl | Cl | 130 |
| 28 | 3,4,5-(OCH₃)₃ phenyl | Cl | 180 |
| 29 | 2-CH₃phenyl | Cl | 160 |
| 30 | 3-Cl phenyl | Cl | 220 |
| 31 | 3,4-(CH₃)₂ phenyl | Cl | 185 |
| 32 | cyclopentyl | Cl | 150 |
| 33 | cyclohexyl | Cl | 205–209 |
| 34 | 2-F phenyl | Br | 195 |
| 35 | 2,4-Cl₂phenyl | Cl | 160 |
| 36 | 4-C(CH₃)₃ phenyl | Cl | 147 |
| 37 | 2-Cl,6-F phenyl | Cl | 115 |
| 38 | 4-OCH₃ phenyl | Cl | 138 |
| 39 | 2-CF₃ phenyl | Cl | 128 |
| 40 | 4-Br phenyl | Br | 228–230 |
| 41 | 2-Cl,6-F phenyl | Br | 170 |
| 42 | 4-CF₃phenyl | Br | 246 |
| 43 | 3-F phenyl | Br | 254 |
| 44 | 2-CF₃ phenyl | Br | 192 |
| 45 | 2-F phenoxy | Cl | 145 |
| 46 | 2-CH₃ phenoxy | Cl | 152 |
| 47 | 2-Cl phenoxy | Cl | 178–182 |
| 48 | 2,6-(CH₃)₂ phenoxy | Cl | 144–146 |
| 49 | 3-CH₃ phenoxy | Cl | 135–137 |
| 50 | ethoxy | Cl | 102–105 |
| 51 | isopropyl | Cl | 135–137 |
| 52 | isobut-3-yl | Cl | 120–122 |

EXAMPLE 53

The fungicidal activity of compounds of the invention was investigated by means of the following tests.

(a) Antisporulant activity against vine downy mildew (*Plasmopara viticola*; PVA)

The test is a direct antisporulant one using a foliar spray. The lower surface of leaves of whole vine plants (cv Cabernet Sauvignon) are inoculated by spraying with an aqueous suspension containing 2.5×10⁴ zoosporangia/ml two days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 1000 ppm, and the spray volume is 700 l/ha. After spraying, the plants are returned to normal glasshouse conditions for 96 hours and are then transferred to the high humidity cabinet for 24 hours to induce sporulation, prior to assessment. Assessment is based on the percentage of the leaf area covered by sporulation compared with that on control leaves.

(b) Direct protectant activity against tomato late blight (*Phytophthora infestans*: PIP)

The test is a direct protectant one using a foliar spray. The upper leaf surfaces of tomato plants with two expanded leaves (cv. First in the field) are sprayed with the test compound at a dosage of 1000 ppm using a sprayer as described under (a). After a subsequent period of 24 hours under normal glasshouse conditions, the upper surfaces of the leaves are inoculated by spraying with an aqueous suspension containing 2×10⁵ zoospores/ml. The inoculated plants are kept for 24 hours in a high humidity cabinet and 5 days under growth chamber conditions. The assessment is based on the percentage of diseased leaf area compared with that on control leaves.

(c) Direct protectant activity against vine downy mildew (*Plasmopara viticola*: PVP)

The test is a direct protectant one using a foliar spray. The lower surface of leaves of whole vine plants (cv Cabernet Sauvignon) are sprayed with the test compound at a dosage of 1000 ppm using an automated sprayline as described under (a), and after a subsequent period of 24 hours under normal glasshouse conditions the lower surfaces of the leaves are inoculated by spraying with an aqueous suspension containing 2.5×10⁴ zoosporangia/ml. The inoculated plants are kept for 24 hours in a high humidity cabinet, 5 days under normal glasshouse conditions and then returned for a further 24 hours to high humidity. Assessment is based on the percentage of leaf area covered by sporulation compared with that on control leaves.

(d) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"—Trade Mark). One day after treatment the seedlings are inoculated by spraying the leaf upper surfaces with a suspension of *A. solani* conidia containing 10⁴ spores/ml. For 4 days after inoculation plants are kept moist in a humidity compartment at 21° C. Disease is assessed 4 days after inoculation, based on the percentage of leaf surface area covered by lesions.

(e) Direct protectant activity against broad bean grey mould (*Botrytis cinerea*; BCB)

The test is a direct protectant one using a foliar spray. The upper surfaces of leaves of broad bean plants (cv The Sutton) are sprayed with the test compound at a dosage of 1000 ppm using an automated sprayline as described under (a). 24 hours after spraying the leaves are inoculated with an aqueous suspension containing 10⁵ conidia/ml. For 4 days after inoculation plants are kept moist in a humidity compartment at 21° C. Disease is assessed 4 days after inoculation, based on the percentage of leaf surface area covered by lesions.

(f) Activity against wheat leafspot (*Leptosphaeria nodorum*; LN.)

The test is a direct therapeutic one, using a foliar spray. Leaves of wheat plants (cv Norman), at the single leaf stage, are inoculated by spraying with an aqueous suspension containing 1×10⁶ spores/ml. The inoculated plants are kept for 24 hours in a high humidity compartment prior to treatment. The plants are sprayed with a solution of the test compound at a dosage of 1000 ppm using an automated sprayline as described under (a). After drying, the plants are kept for 6–8 days at 22° C. and moderate humidity, followed by assessment. Assessment is based on the density of lesions per leaf compared with that on leaves of control plants.

(g) Activity against wheat brown rust (*Puccinia recondita*; PR)

The test is a direct protectant one using a foliar spray. Wheat seedlings (cv Avalon) are grown to the 1–1½ leaf stage. The plants are then sprayed with the test compound at a dosage of 1000 ppm using an automated sprayline as described under (a). Test compounds are applied as solutions or suspensions in a mixture of acetone and water (50:50 v/v) containing 0.04% surfactant ("TWEEN 20"—Trade Mark). 18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C. The disease is assessed 10 days after inoculation on the basis of the percentage of the plant covered by sporulating pustules compared with that on the control plants.

(h) Activity against barley powdery mildew (*Erysiphe graminis* f.sp. hordei; EG)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1000 ppm using an automated sprayline as described under (a). After drying, plants are returned to a compartment at 20°–25 ° C. and moderate humidity for up to 7 days, followed by assessment. Assessment is based on the percentage of leaf area covered by sporulation compared with that on leaves of control plants.

(i) Activity against rice leaf blast (*Pyricularia oryzae*; PO)

The test is a direct therapeutic one using a foliar spray. The leaves of rice seedlings (cv Aichiaishi—about 30 seedlings per pot) are sprayed with an aqueous suspension containing $10^5$ spores/ml 20–24 hours prior to treatment with the test compound. The inoculated plants are kept overnight in high humidity and then allowed to dry before spraying with the test compound at a dosage of 1000 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

(j) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 50 ppm compound and 2.5% acetone. Each compartment is inoculated with a 6 mm diameter plug of agar/mycelium taken from a 14 day old culture of *P. herpotrichoides*. Plates are incubated at 20° C. for 12 days until the assessment of mycelial growth.

(k) Activity against Fusarium in-vitro (*Fusarium culmorum*; FSI)

This test measures the in vitro activity of compounds against a species of *Fusarium* that causes stem and root rots. The test compound is dissolved or suspended in acetone and added to molten half strength Potato Dextrose Agar to give a final concentration of 50 ppm compound and 2.5% acetone. After agar has set, plates are inoculated with 6 mm diameter plugs of agar and mycelium taken from a 7 day old culture of *Fusarium* sp. Plates are incubated at 20 ° C. for 5 days and radial growth from the plug is measured.

The extent of disease control in all the above tests is expressed as a rating compared with either an untreated control or a diluent-sprayed-control, according to the criteria:

0=less than 50% disease control
1=about 50–80% disease control
2=greater than 80% disease control The results of these tests are set out in Table II below:

TABLE II

| Example No. | PVA | PIP | PVP | AS | BCB | LN | PR | EG | PO | PHI | FSI |
|---|---|---|---|---|---|---|---|---|---|---|---|
| 1 |  | 1 |  | 1 | 2 |  | 2 |  |  | 2 | 2 |
| 4 |  |  | 1 | 1 | 2 |  | 1 |  |  | 2 | 2 |
| 5 |  |  | 2 | 2 | 2 |  | 1 |  |  | 2 | 2 |
| 7 |  |  |  | 1 | 1 |  | 2 |  |  | 2 | 2 |
| 8 |  | 2 |  |  | 2 |  | 2 |  | 1 | 2 | 2 |
| 9 |  | 1 |  | 2 | 2 |  | 2 |  |  | 2 | 2 |
| 1o |  |  |  | 2 | 2 |  | 2 |  |  | 2 | 1 |
| 11 |  | 2 |  |  | 2 |  | 2 |  |  | 2 | 2 |
| 12 |  | 2 |  |  | 2 |  | 2 |  |  |  | 1 |
| 13 |  |  |  |  |  |  |  |  |  | 2 | 2 |
| 14 |  |  |  |  |  |  |  |  |  | 2 | 1 |
| 15 |  | 2 |  | 1 | 2 | 1 | 1 |  |  |  |  |
| 16 |  | 2 |  | 2 | 1 |  |  |  |  | 2 | 2 |
| 17 |  | 2 |  | 2 | 2 |  |  |  |  | 2 | 2 |
| 18 |  | 2 |  | 2 | 2 |  |  |  |  | 2 | 2 |
| 19 |  | 2 |  | 2 |  |  |  |  |  | 2 | 2 |
| 20 | 2 |  |  |  | 2 |  | 2 |  |  | 1 |  |
| 21 |  | 2 |  | 2 |  |  |  |  |  | 2 | 2 |
| 23 |  |  |  | 2 | 2 |  |  |  |  | 1 | 1 |
| 24 |  |  |  | 2 | 2 | 1 |  |  |  | 2 | 2 |
| 25 |  |  |  | 1 | 1 | 1 |  |  |  |  | 1 |
| 26 |  |  |  | 1 | 2 |  |  | 1 |  | 2 | 2 |

EXAMPLE 54

The fungicidal activity of compounds of the invention was litigated by means of the following tests.

(a) Antisporulant activity against vine downy mildew (*Plasmopara viticola*; PVA)

The test is a direct antisporulant one using a foliar spray. The lower surface of leaves of vine plants (cv. Cabernet Sauvignon), approximately 8 cm high, are inoculated with an aqueous suspension containing $5 \times 10^4$ zoosporangia/ml. The inoculated plants are kept for 24 hours at 21° C. in a high humidity cabinet, then for 24 hours in a glasshouse at 20° C. and 40% relative humidity. Infected leaves are sprayed on their lower surfaces with a solution of the test compound in 1:1 water/acetone containing 0.04% "TWEEN 20" (Trade Mark; a polyoxyethylene sorbitan ester surfactant). Plants are sprayed using a track sprayer equipped with 2 air-atomising nozzles. The concentration of the compound is 600 ppm and the spray volume is 750 l/ha. After drying, the plants are returned to the glasshouse at 20° C. and 40% relative humidity for 96 hours and are then transferred to the high humidity cabinet for 24 hours to induce sporulation. Assessment is based on the percentage of the leaf area covered by sporulation compared with that on control leaves.

(b) Direct protectant activity against tomato late blight (*Phytophthora infestans*; PIP)

The test is a direct protectant one using a foliar spray. Tomato plants with two expanded leaves (cv. First in the Field) are sprayed with the test compound at a dosage of 600 ppm as described under (a). After drying, the plants are kept for 24 hours in a glasshouse at 20° C. and 40% relative humidity. The upper surfaces of the leaves are then inoculated with an aqueous suspension containing $2 \times 10^5$ zoosporangia/ml. The inoculated plants are kept for 24 hours at 18° C. in a high humidity cabinet and then for 5 days in a growth chamber at 15° C. and 80% relative humidity with 14 hours light/day. The assessment is based on the percentage of diseased leaf area compared with that on control leaves.

(c) Activity against tomato early blight (*Alternaria solani*; AS)

The test is a direct prophylactic one using a foliar spray. Tomato seedlings (cv Outdoor Girl), at the stage at which the second leaf is expanded, are sprayed with the test compound at a dosage of 600 ppm as described under (a). After drying, the plants are kept for 24 hours in a glasshouse at 20° C. and 40% relative humidity followed by inoculation of the leaf upper surfaces with an aqueous suspension of *A. solani* conidia containing $1 \times 10^4$ conidia/ml. After 4 days in a high humidity cabinet at 21° C., disease is assessed based on the percentage of leaf surface area covered by lesions when compared with control plants.

(d) Direct protectant activity against broad bean grey mould (*Botrytis cinerea*; BCB)

The test is a direct protectant one using a foliar spray. Broad bean plants (cv The Sutton) with two leaf pairs are sprayed with the test compound at a dosage of 600 ppm as described under (a). After drying, the plants are kept for 24 hours in a glasshouse at 20° C. and 40% relative humidity. The upper surface of the leaves are then inoculated with an aqueous suspension containing $1 \times 10^6$ conidia/ml. Plants are kept for 4 days at 22° C. in a high humidity cabinet. The assessment is based on the percentage of diseased leaf area compared with that on control leaves.

(e) Activity against wheat leafspot (*Leptosphaeria nodorum*; LN)

The test is a direct therapeutic one using a foliar spray. Wheat seedlings (cv Norman), at the single leaf stage, are inoculated with an aqueous suspension containing $1.5 \times 10^6$ conidia/ml. The inoculated plants are kept for 24 hours at 20° C. in a high humidity cabinet, followed by spraying with the test compound as described under (a). After drying, the plants are kept for 6–8 days in the glasshouse at 22° C. and 70% relative humidity. Assessment is based on the density of lesions per leaf compared with that on leaves of control plants.

(f) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 10 ppm test compound and 0.825% acetone. The fungal inoculum consists of mycelial fragments of *P. herpotrichoides* grown in half strength Potato Dextrose Broth in shaken flasks and added to the broth to provide $5 \times 10^4$ mycelial fragments/ml broth. Petri dishes are incubated at 20° C. for 10 days until the assessment of mycelial growth.

(g) Activity against Rhizoctonia in-vitro (*Rhizoctonia solani*; RSI)

The test measures the in-vitro activity of compounds against *Rhizoctonia solani* that causes stem and root rots. The test compound is dissolved or suspended in acetone and added into 4 ml aliquots of half strength Potato Dextrose Broth dispensed in 25-compartment petri dishes to give a final concentration of 10 ppm compound and 0.825% acetone. The fungal inoculum consists of mycelial fragments of *R. solani* grown in half strength Potato Dextrose Broth in shaken culture flasks and added to the broth to provide $5 \times 10^4$ fragments/ml broth. Petri dishes are incubated at 20° C. for 10 days until the assessment of mycelial growth.

(h) Activity against apple scab in-vitro (*Venturia inaegualis*; VII)

This test measures the in-vitro activity of compounds against *Venturia inaegualis* that causes apple scab. The test compound is dissolved or suspended in acetone and added into 4 ml aliquots of half strength Potato Dextrose Broth dispensed in 25-compartment petri dishes to give a final concentration of 10 ppm compound and 0.825% acetone. The fungal inoculum consists of mycelial fragments and spores of *V. inaegualis* grown on malt agar and added to the broth to provide $5 \times 10^4$ propagules/ml broth. Petri dishes are incubated at 20° C. for 10 days until the assessment of mycelial growth.

The extent of disease control in all the above tests is expressed as a rating compared with either an untreated control or a diluent-sprayed-control, according to the criteria:

0=less than 50% disease control
1=50–80% disease control
2=greater than 80% disease control The results of these tests are set out in Table III below:

TABLE III

| Example No. | PVA | PIP | AS | BCB | LN | PHI | RSI | VII |
|---|---|---|---|---|---|---|---|---|
| 27 | | | 2 | 1 | | | 2* | 2* |
| 28 | | 2 | 2 | 2 | | 2* | 2* | 2* |
| 29 | 1 | | 1 | 2 | | 2* | 2* | 2* |
| 30 | | | 2 | 2 | | 2* | 2* | 2* |

TABLE III-continued

| Example No. | PVA | PIP | AS | BCB | LN | PHI | RSI | VII |
|---|---|---|---|---|---|---|---|---|
| 31 | | | 1 | 2 | | 2* | 2* | 2* |
| 32 | | 2 | 2 | 1 | | 2* | 2* | |
| 33 | | 2 | 2 | 2 | | 2* | 2* | |
| 34 | | 2 | 2 | | | 2 | 1 | 2 |
| 35 | | 2 | | | 1 | 2 | 1 | 2 |
| 36 | | 1 | | | | 2 | 2 | 2 |
| 37 | | | 1 | 1 | | 2 | | 2 |
| 38 | | | | 2 | | 2 | 1 | 2 |
| 39 | | 2 | | | | 2 | | 2 |
| 40 | | 2 | 2 | 2 | | 2 | 1 | 2 |
| 2 | | 2 | | 2 | 1 | 2 | | 2 |

*signifies dosage of test compound = 30 ppm

EXAMPLE 55
Determination of MIC-Values of compounds against various phytopathogenic fungi The MIC (Minimum Inhibition Concentration)-values were determined by serial dilution tests using 48-well microtitre plates. The dilution of the test compounds in the nutrient solution and the distribution to the wells were carried out by a TECAN RSP 5000 robotic sample processor.

The compounds were diluted to the following concentrations: 100, 50, 25, 12.5, 6.25, 3.13, 1.56, 0.78, 0.39, 0.20, 0.10 and 0.05 µg/ml.

For preparation of the nutrient solution, V8 juice (Trade Mark) was neutralised with calcium carbonate and centrifuged. The supernatant was diluted with distilled water (1:5) to the final concentration.

The fungi (*Alternaria solani, Botrytis cinerea, Pseudocercosporella herpotrichoides, Micronectriella nivalis, Gaeumannomyces graminis*) were added into the wells as a droplet of spore suspension. The microtitre plates were then incubated at 20° C. for 6–8 days. The MIC-value, which was defined to be the lowest concentration in the dilution series without mycelial growth, was determined by visual inspection of the plates.

The results of these tests are set out in Table IV below:

TABLE IV

| Ex. No. | Alternaria solani | Botrytis cinerea | MIC-value (ppm) Pseudocercosporella herpotrichoides | Micronectriella nivalis | Gaeumannomyces graminis |
|---|---|---|---|---|---|
| 1 | | | 25.0 | 1.56 | 3.13 |
| 3 | | | 6.25 | 0.78 | 0.20 |
| 6 | | >100.0 | | | |
| 9 | | | 12.5 | 0.78 | 0.10 |
| 11 | | | 3.13 | 0.39 | 0.20 |
| 13 | | | >100.0 | 6.25 | 0.39 |
| 14 | | | 25.0 | 6.25 | 0.78 |
| 17 | | | 25.0 | 12.5 | 0.78 |
| 19 | | | 12.5 | 6.25 | 0.10 |
| 26 | | | 6.25 | 0.78 | 0.39 |
| 29 | | | 12.5 | 6.25 | 1.56 |
| 31 | | | 12.5 | 3.13 | 0.78 |
| 35 | | | 6.25 | 0.39 | 0.39 |
| 36 | | | 3.13 | 0.39 | 0.78 |
| 41 | 50.0 | 25.0 | | | |
| 42 | >100.0 | >100.0 | | | |
| 43 | >100.0 | >100.0 | | | |
| 44 | >100.0 | >100.0 | | | |

EXAMPLE 56
Determination of the Minimum Inhibitory Concentration of Test Compounds in the Serial Dilution Test with Phytopathogenic Fungi *Alternaria solani, Botrytis cinerea, Rhizoctonia solani*

The serial dilution test was carried out using Microtiter test with 24 or 48 wells per plate. The test compounds were used a 1000 µg/ml aqueous stock suspension containing 20% acetone which was then sterile filtered in a 0.2µ filter. The dilution of the sterile fungicide suspension with the nutrient solution and the subsequent pipetting into the different wells was carried out using a TECAN RSP 5000 Robotic Sample Processor. The concentrations tested ranged from 100 µg/ml down to 0.05 µg/ml. 12 Dilution steps were made. The nutrient solution was chosen according to the nutrient requirements of the pathogen.

The inoculum was added as a droplet (50 µl) of a spore suspension ($5\times10^8$/ml) into the wells.

Assessment

After 6–12 days incubation at suitable temperatures, the MIC value was determined by visual estimation. The lowest concentration in the dilution row without mycelial growth was defined as the MIC value. The results are set out in Table V below:

TABLE V

| Example No. | Alternaria solani | MIC-value (ppm) Botrytis cinerea | Rhizootonia solani |
|---|---|---|---|
| 48 | 25.0 | >100.0 | >100.0 |
| 49 | 25.0 | 6.25 | >100.0 |
| 50 | 12.5 | 25.0 | 100.0 |
| 51 | 12.5 | 12.5 | 25.0 |

EXAMPLE 57
Field Pot Test with *Cercospora arachidicola* on Peanuts

15 Seeds of peanuts were sown in pots filled with a soil substrate. When the plants have developed 4 true leaves (approx. 12–14 days after seeding) the fungicides and the test compounds were applied using a hand sprayer. The test compounds were applied at a concentration of 500 µg/ml in a spraywash containing 10% acetone and 0.05% Triton X 155 in water. The total amount of spraywash corresponded to 1000 l/ha. Six replicates (pots) per treatment were used. 2 days after treatment the pots were exposed to peanut plants in the field on which the fungus, *Cercospora arachidicola*, had formed sporulating lesions. The assessment was carried out 15 days after treatment by estimating the percentage of infected leaf area. The % efficacy was calculated using the Abbott formula.

Field pot test with *Puccinia arachidis* on Peanuts 15 seeds of peanuts were sown in pots filled with a soil substrate. When the plants have developed 4 true leaves the fungicides and the test compounds were applied using a hand sprayer. The test compounds were applied at a concentration of 500 µg/ml in a spraywash containing 10% acetone and 0.05% Triton X 155 in water. The total amount of spraywash corresponded to 1000 l/ha. Six replicates per treatment were used. 2 Days after treatment the pots were exposed to peanut plants in the field on which the fungus, *Puccinia arachidis*, had formed sporulating pustules on the leaves. The assessment was carried out 19 days after treatment by estimating the percentage of infected leaf area. The % efficacy was calculated using the Abbott formula.

RESULTS

The results are set out in Table VI below:

TABLE VI

| Example No. | % efficacy | |
|---|---|---|
| | *Fuccinia arachidis* | *Cercospora arachidicola* |
| 7 | 25 | 58 |
| 8 | 17 | 33 |
| 9 | 25 | 50 |
| 11 | 25 | 33 |
| 12 | 33 | 67 |
| 16 | 42 | 50 |
| 25 | 42 | 25 |
| 38 | 42 | 42 |

We claim:

1. A fungicidal composition which comprises a carrier and, as active ingredient, a compound of the formula

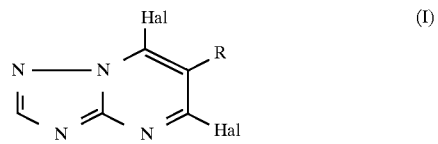

in which
R represents an optionally substituted branched or straight-chain alkyl, or alkoxy group, or an optionally substituted cycloalkyl, aryl, aryloxy or heterocyclic group, and Hal represents a fluorine, chlorine, bromine or iodine atom.

2. A composition according to claim 1 in which R represents a propyl, butyl, ethoxy, cyclopentyl, cyclohexyl, fluorophenyl, chlorophenyl, bromophenyl, dichlorophenyl, chloro-fluorophenyl, methylphenyl, propylphenyl, butylphenyl, dimethylphenyl, trifluoromethylphenyl, methoxyphenyl, ethoxyphenyl, dimethoxyphenyl, diethoxyphenyl, trimethoxyphenyl, trifluoromethoxyphenyl, chlorosulphonylphenyl, biphenylyl, phenoxyphenyl, benzyloxyphenyl, fluorophenoxy, chlorophenoxy, methylphenoxy, dimethylphenoxy, naphthyl or thienyl group; and Hal represents a chlorine or bromine atom.

3. A composition according to claim 1 which comprises at least two carriers, at least one of which is a surface active agent.

4. A compound of the general formula I as defined in claim 1 with the provisos that,
  (i) when R represents an optionally substituted aryl group, then both groups Hal do not represent a chlorine atom or both groups Hal do not represent a bromine atom; and
  (ii) when R represents a methyl group, then both groups Hal do not represent a chlorine atom.

5. A compound according to claim 4 as named in any one of Examples 26, 27, 32, 33, and 45 to 52.

6. A process for the preparation of a compound of formula I as defined in claim 4 which comprises
  (a) reacting a compound of the general formula

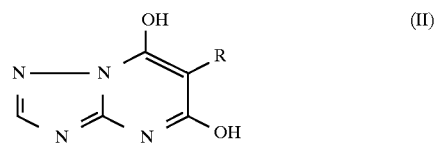

in which R is as defined in claim 4, with a chlorinating or brominating agent to produce a compound of formula I in which Hal represents a chlorine or bromine atom;

(b) if desired, reacting the compound of formula I formed in (a) with a fluorinating agent to produce a compound of formula I in which Hal represents a fluorine atom; and
  (c) if desired, reacting the compound of formula I formed in (a) with $NH_3$ and then with diiodomethane in the presence of a diazotising agent to produce a compound of formula I in which at least one Hal represents an iodine atom.

7. A process according to claim 6 substantially as hereinbefore described and with reference to Example 1 or Example 2.

8. A compound of formula I whenever prepared by a process according to claim 6.

9. A method of combating fungus at a locus which comprises treating the locus with a compound of formula I as defined in claim 1; or with a composition as defined in claim 1.

10. A method according to claim 9 in which the locus comprises plants subject to or subjected to fungal attack, seeds of such plants or the medium in which the plants are growing or are to be grown.

11. A composition according to claim 1 wherein R is selected from the group consisting of 2-chlorophenyl, 4-$OC_2H_5$ phenyl, 3-$OCH_3$ phenyl, 2-$OCH_3$ phenyl, 2-$SO_2Cl$ phenyl, 3-$CF_3$ phenyl, 4-$CH(CH_3)_2$ phenyl, 4-$OCF_3$ phenyl, naphth-2-yl, 4-F phenyl, 4-$OC_6H_5$ phenyl, 4-biphenylyl, 3,4-$(OCH_3)_2$ phenyl, 4-$OCH_2C_6H_5$ phenyl, 2-F phenyl, 3-F phenyl, 2- Br phenyl, 4-Br phenyl, 2-$OCH_2C_6H_5$ phenyl, 2,3-$(OCH_3)_2$ phenyl, 3-Br phenyl, naphth-1-yl, 2,3-$(OC_2H_5)_2$ phenyl, 3,4-$Cl_2$ phenyl, 3,4,5-$(OCH_3)_3$ phenyl, 2-$CH_3$ phenyl, 3-Cl phenyl, 3,4-$(CH_3)_2$ phenyl, 2-F phenyl, 2,4-$Cl_2$ phenyl, 4-$C(CH_3)_3$ phenyl, 2-Cl, 6-F phenyl, 4-$OCH_3$ phenyl, 2-$CF_3$ phenyl, 4-Br phenyl, 2-Cl, 6-F phenyl, 4-$CF_3$ phenyl, 3-F phenyl and 2-$CF_3$ phenyl.

12. A compound according to claim 4, wherein R is thien-2-yl.

13. A compound according to claim wherein 4, wherein R is thien-3-yl.

14. A compound according to claim herein 9, wherein R is cyclopentyl.

15. A compound according to claim 4, wherein R is cyclohexyl.

16. A compound according to claim 4, wherein R is 2-F phenoxy.

17. A compound according to claim 9, wherein R is 2-$CH_3$ phenoxy.

18. A compound according to claim 4, wherein R is 2-Cl phenoxy.

19. A compound according to claim 4, wherein R is 2,6-$(CH_3)_2$ phenoxy.

20. A compound according to claim 4, wherein R is 3-$CH_3$ phenoxy.

21. A compound according to claim 4, wherein R is ethoxy.

22. A compound according to claim 4, wherein R is isopropyl.

23. A compound according to claim 4, wherein R is isobut-3-yl.

* * * * *